(12) United States Patent
Beacham et al.

(10) Patent No.: US 10,408,947 B2
(45) Date of Patent: Sep. 10, 2019

(54) DIRECT ATTACHED TUNGSTEN 3-D PRINTED COLLIMATOR TO SCINTILLATOR ARRAY

(71) Applicant: General Electric Company, Schenectady, NY (US)

(72) Inventors: Jimmie Autrey Beacham, Waukesha, WI (US); Rui Guo, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 167 days.

(21) Appl. No.: 15/257,397

(22) Filed: Sep. 6, 2016

(65) Prior Publication Data

US 2018/0064407 A1    Mar. 8, 2018

(51) Int. Cl.
*A61B 6/00* (2006.01)
*G01T 1/20* (2006.01)
*A61B 6/03* (2006.01)

(52) U.S. Cl.
CPC .......... *G01T 1/2002* (2013.01); *G01T 1/2018* (2013.01); *A61B 6/032* (2013.01); *A61B 6/4291* (2013.01)

(58) Field of Classification Search
CPC .. A61B 6/032; A61B 6/06; A61B 6/54; A61B 6/4233; A61B 6/4258; A61B 6/502; A61B 6/4014; A61B 6/4488; A61B 6/4291; A61B 6/482; A61B 6/583; A61B 6/505; A61B 6/5205; A61B 2090/0436; A61B 2090/0481; A61B 2562/164; A61B 5/0088; A61B 5/682; G01T 1/2002; G01T 1/2018; G01T 1/202; G01T 1/20; G03F 7/0017; G21K 1/02; G21K 1/00; G01N 2223/419; G01N 23/046; G01N 2021/1761; G01N 21/17; G01N 21/55; G01V 5/0016; G01V 5/005; H05G 1/70
USPC ............................. 378/4, 19, 62, 98, 8, 147
See application file for complete search history.

(56) References Cited

U.S. PATENT DOCUMENTS

| | | | |
|---|---|---|---|
| 7,112,797 B2 | 9/2006 | Hoge | |
| 7,310,405 B2 | 12/2007 | Venkataramani et al. | |
| 7,329,875 B2* | 2/2008 | McEvoy | G01T 1/20 250/367 |
| 2002/0131547 A1* | 9/2002 | Riedner | G01T 1/202 378/19 |

(Continued)

*Primary Examiner* — Irakli Kiknadze
(74) *Attorney, Agent, or Firm* — Boyle Fredrickson, S.C.

(57) ABSTRACT

In the present invention, an integrated scintillator and collimator array for a detector utilized in a CT imaging system is provided. The integrated scintillator and collimator assembly is are fabricated from a manufacturing process or technique in which a scintillator array including a number of scintillation pixels is optically measured to determine the precise position of each pixel on the array. A transition material is applied to the array in a 3D printing method using the position data from the optical measurement and in subsequently bonded thereto in a sintering process to form a transition material layer. A collimator material is then 3D printed onto the transition material layer using the optical measurement data to form collimator plates on the array in alignment with the pixels thereby forming a unitary scintillator/collimator assembly for use in a detector for a CT imaging system.

18 Claims, 7 Drawing Sheets

(56) References Cited

U.S. PATENT DOCUMENTS

2004/0217291 A1* 11/2004 Hoge .................... G01T 1/1648
250/363.1
2006/0033030 A1* 2/2006 Ito ......................... G01T 1/2018
250/370.11
2015/0316659 A1* 11/2015 Okamura .............. G01T 1/2018
250/367

* cited by examiner

DIRECT ATTACHED TUNGSTEN 3-D PRINTED COLLIMATOR TO SCINTILLATOR ARRAY

BACKGROUND OF INVENTION

The invention relates generally to diagnostic imaging and, more particularly, to an integrated scintillator and collimator and method of manufacturing same.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

As stated above, typical x-ray detectors include a collimator for collimating x-ray beams such that collection of scattered x-rays is minimized. As such, the collimators operate to attenuate off-angle scattered x-rays from being detected by a scintillator cell. Reducing this scattering reduces noise in the signal and improves the final reconstructed image. Therefore, it is necessary that the scintillator array and the collimator, typically plates extending along one dimension above the scintillator array, are precisely and uniformly aligned. That is, exact mechanical alignment is required between the collimator plates and the cast reflector lines in the array of scintillators.

To accomplish this, known manufacturing processes attempt this exact alignment by constructing a continuous collimator that is sized to dimensionally match the width and length of the entire detector array. That is, the collimator plates are arranged or arrayed in a continuous consistent pattern or pitch that spans the entire detector length and is placed and attached to the detector rail structure. As such, individual scintillator arrays or packs are must then be exactly aligned to the continuous collimator to ensure that all scintillator cells and collimator cells are aligned exactly; otherwise the collimator must be discarded or repaired, or the scintillator packs must be discarded. This process requires excessively tight tolerancing and requires great operator skill and patience to manually assemble the collimators to the scintillators to form the detector. Accordingly, these known processes are susceptible to waste of parts, material, and labor. Further, as the problem of the alignment of the collimator between the x-ray focal spot and the individual detector components currently is addressed only by maintaining tight tolerances in the hand assembled collimator/scintillator structures, the preservation of tight tolerances during the assembly process causes a great deal of cost and low yield during image quality testing of the resulting structures.

Additionally, as CT detectors grow in the z-direction, alignment requirements will tighten and the number of cells requiring alignment will increase. Therefore, the low process yields and high-end process scrap and re-work associated with these known manufacturing processes will increase the cost and time associated with CT detector assembly.

Therefore, it would be desirable to design an integrated scintillator and collimator assembly that includes precise alignment of the components as well as a method of manufacturing such an integrated scintillator and collimator that reduces the time and cost to provide the precisely aligned components.

BRIEF DESCRIPTION OF THE INVENTION

There is a need or desire for an improved collimator and scintillator assembly and method of manufacturing the assembly that provides precise alignment between the collimator and scintillator in the assembly. In the assembly collimator is built directly on an array of scintillating pixels for use in CT imaging systems. The assembly and method forms the collimator directly on the scintillator array versus on a separate metal base applied to the array. The assembly and method utilizes an optical measurement analysis of the pixels in the array in order to determine the locations for the application of a transition material to the scintillator array. The transition material forms a base on which the material forming the collimator can be applied and/or welded to the scintillator array. The resulting structure combines the scintillator array and the X-ray blocking collimator into one piece with precise alignment of the collimator structures relative to the scintillator pixels and eliminates the time and cost intensive mechanical assembly challenge of manually constructing the collimator and scintillator.

According to one exemplary non-limiting aspect of the invention, a detector includes an array of scintillation pixels, a transition material layer bonded to the pixels and a plurality of collimator plates bonded to the transition material layer.

According to another exemplary non-limiting aspect of the invention, a method of manufacturing a detector having an integrated scintillator and collimator includes the steps of applying a transition material to a scintillator array including scintillator pixels thereon to form a transition material layer on the scintillator array and applying a collimator material to the transition material layer in alignment with the scintillator pixels to form collimator plates on the scintillator array.

According to another exemplary and non-limiting aspect of the invention, an imaging system includes an x-ray source, a control mechanism operably connected to the x-ray source and a detector operably connected to the control mechanism, the detector including a scintillator/collimator assembly having an array of scintillation pixels, a transition material layer bonded to the pixels and a plurality of collimator plates bonded to the transition material layer.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
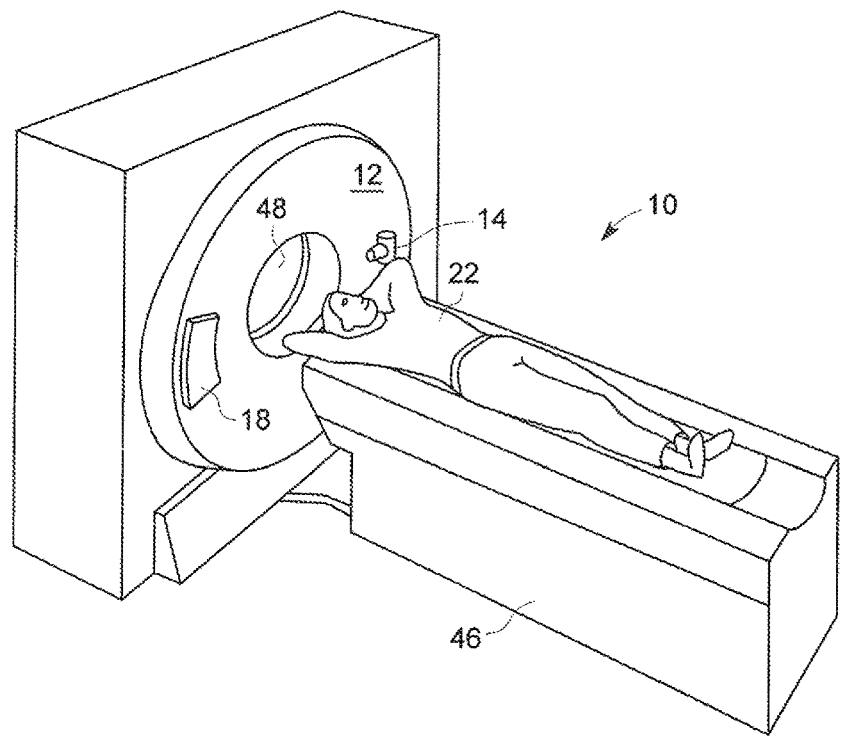
FIG. 1 is a an isometric view of a CT imaging system according to one exemplary non-limiting embodiment of the invention.

Referring to FIG. 1, in the illustrated exemplary non-limiting embodiment, the operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 2:
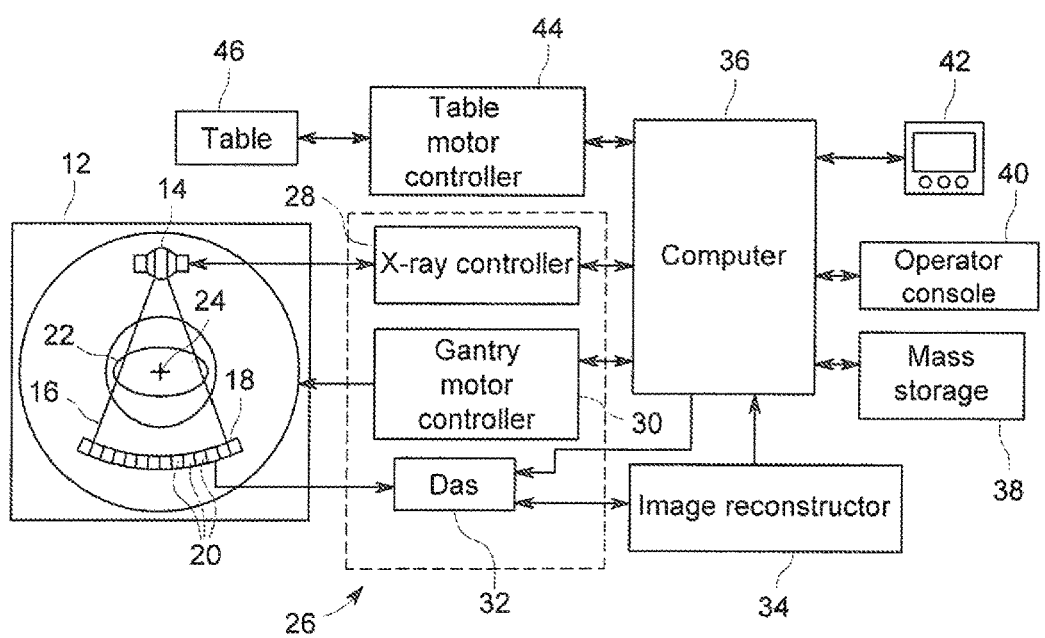
FIG. 2 is a schematic diagram of the CT system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
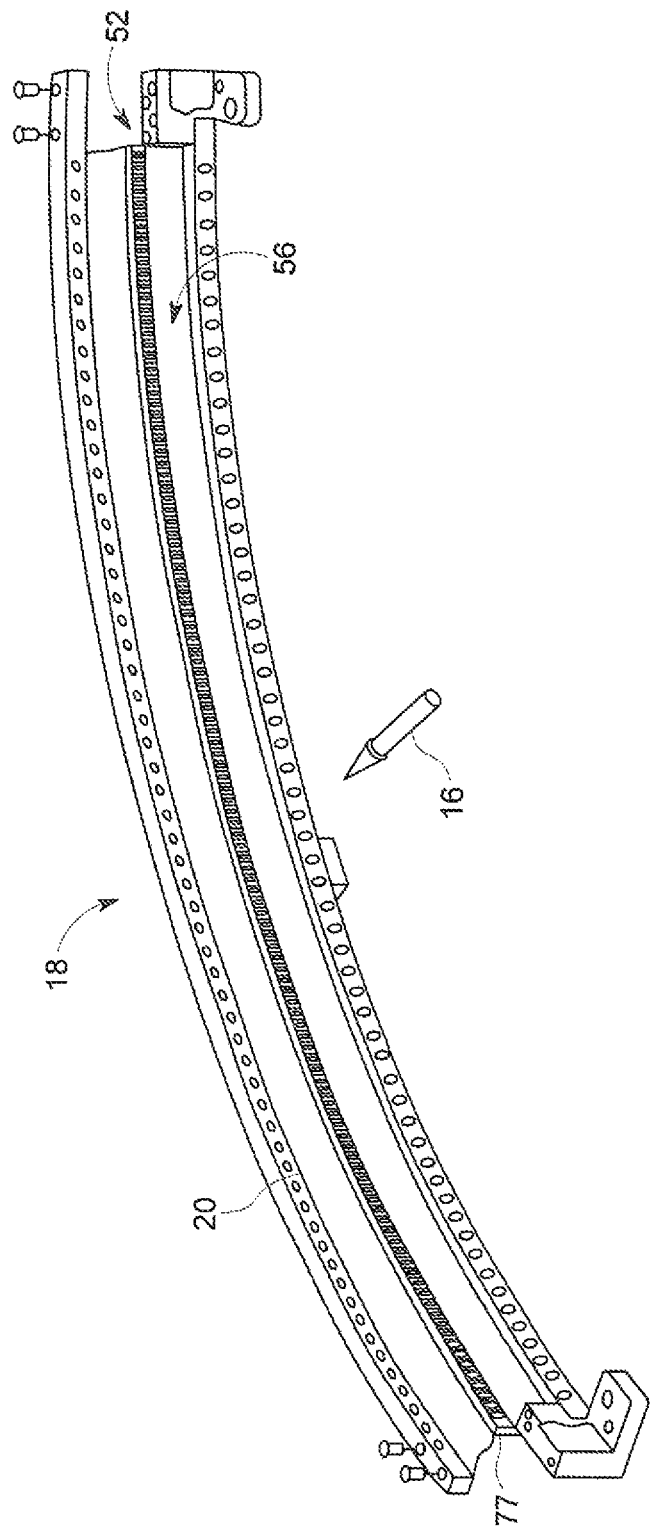
FIG. 3 is an isometric view of a CT system detector array according to one exemplary non-limiting embodiment of the invention.
Figure 4:
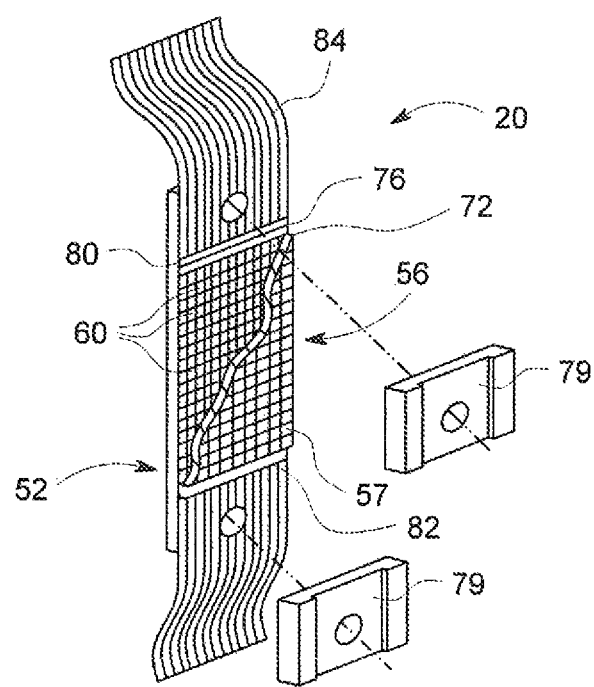
FIG. 4 is am isometric view of one embodiment of a detector of the detector array of FIG. 3 according to one exemplary and non-limiting embodiment of the invention.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, such as that disclosed in U.S. Pat. No. 7,112,797, entitled Scintillator Having Integrated Collimator and Method of Manufacturing Same, which is expressly incorporated by reference herein in its entirety for all purposes, and as shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
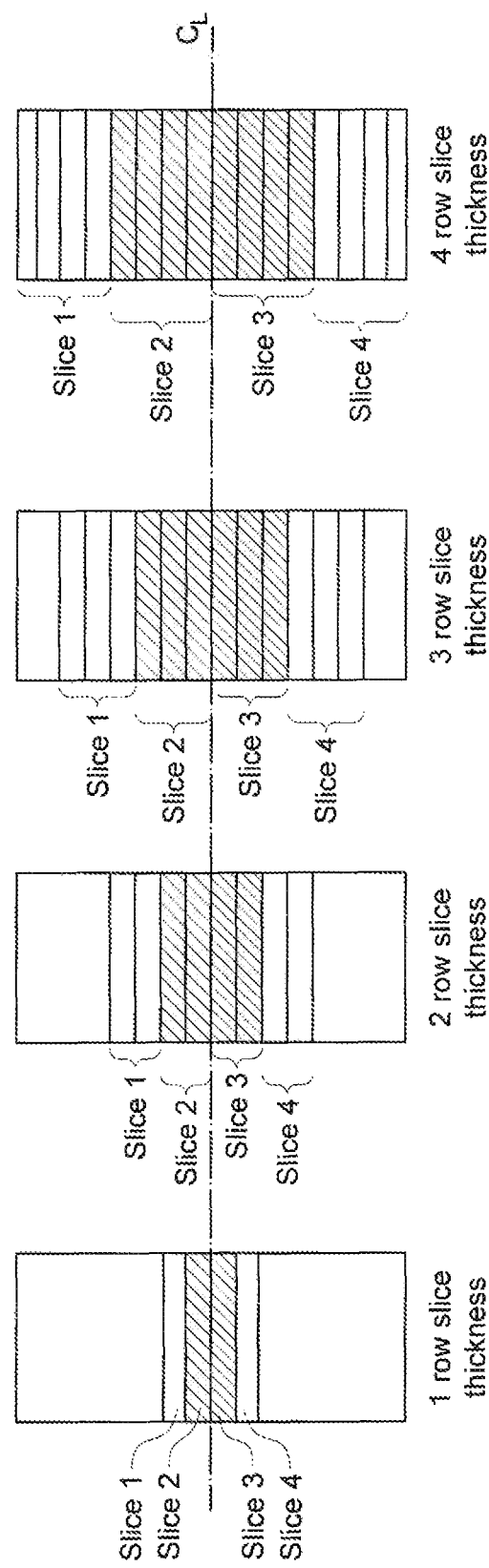
FIG. 5 is illustrative of various configurations of the detector in FIG. 4 in a four-slice mode according to an exemplary non-limiting embodiment of the invention.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
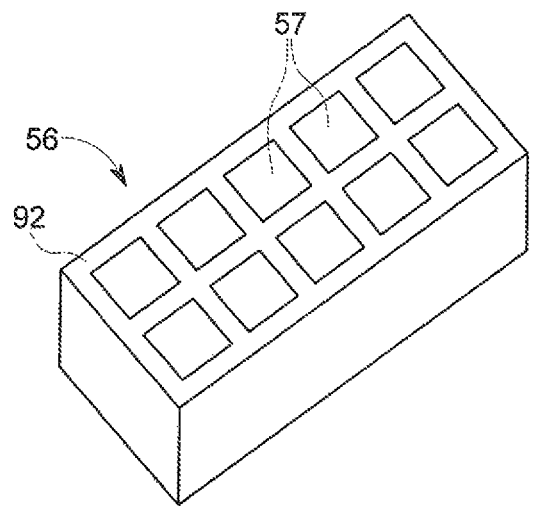
FIG. 6 is an isometric view of a scintillator pack formed according to an exemplary non-limiting embodiment of the invention.

Referring now to FIG. 6, there is depicted a scintillator pack or array 56 of scintillation pixels or elements 57 separated from one another by an X-ray absorbing material 92 that can be cast around the pixels 57 to form the array 56, such as disclosed in U.S. Pat. No. 7,310,405, entitled High-Z Cast Reflector Compositions and Method of Manufacture, which is expressly incorporated by reference herein for all purposes. During the casting, the X-ray absorbing material 92, which can be an epoxy among other suitable materials, flows around the pixels 57 that are pre-positioned in the desired arrangement in order to form the array 56 when the material 92 hardens. In this configuration the pixels 57 are positioned and held in the desired configuration to form the pack or array 56. However, in the casting process various irregularities can be present in the alignment of the pixels 57 with regard to one another due to various factors.

Figure 7:
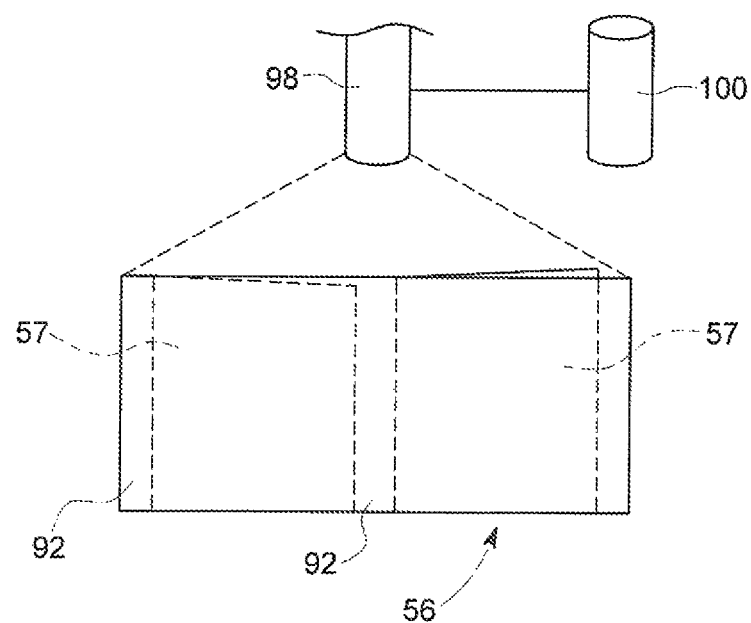
FIG. 7 is an isometric view of a method of optical measurement analysis of a scintillator pack according to an exemplary non-limiting embodiment of the invention

Thus, in order to form a detector 20 or scintillator/collimator assembly 90 with a collimator 110 having collimator plates 108 aligned precisely with the pixels 57 in the pack 56 (FIG. 10), in the method of forming the assembly 90, after formation of the pack/array 56, initially as shown in FIG. 7, the pack 56 is analyzed utilizing an optical measurement system 98, such as Optical Gaging Product, in order to obtain a highly accurate set of data regarding the position of each pixel 57 in the array 56 relative to each of the other pixels 57 and to the material 92 forming the remainder of the pack/array 56. This optical analysis records the position and pitch of each pixel 57 in the array 56 which is recorded in a database 100 operably connected to the optical measurement system 98.

Figure 8:
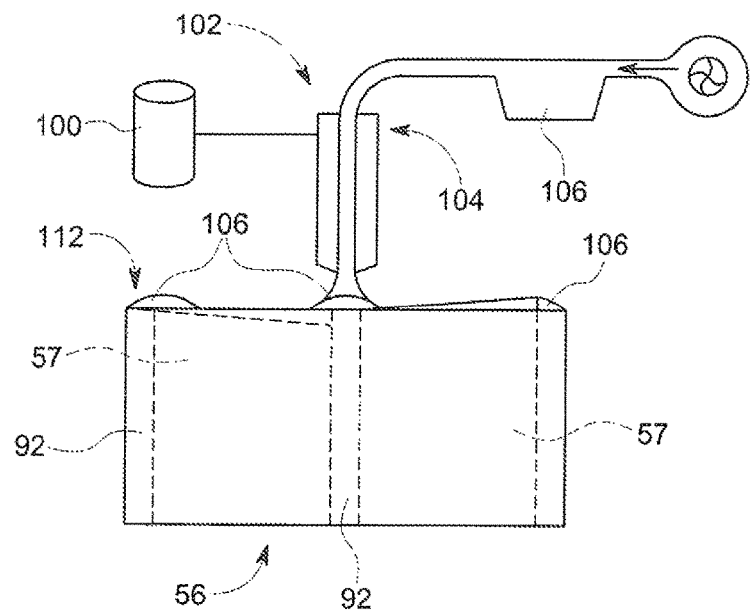
FIG. 8 is a schematic view of a method of application of a transition material to a scintillator pack according to an exemplary non-limiting embodiment of the invention

After the pixels 57 have been measured, as shown in FIG. 8 the pack/array 56 is transported to a computerized numerical control (CNC) device 102 capable of applying a substrate or transition material 106 material onto the array 56 in an adaptive manufacturing technique/process. In one exemplary non-limiting embodiment the device 102 is an aerosol jet style printer 104 that can be operated to accurately deposit a thin layer of the transition material 106 over the array 56. The aerosol jet printer 104 is supplied with the measurement information from the database 100 obtained in the optical analysis of the array 56 in order to enable the printer 104 to determine a spray pattern for the transition material 106 that accurately positions the transition material 106 exiting the printer 104 around the periphery of the pixels 57 in the array 56.

The transition material 106 selected has the properties of being able to: 1) bond to the material forming the pixels 57, which in one exemplary non-limiting embodiment is a ceramic material; 2) be welded to other materials, such as those materials 122 used to form the collimator plates 108; and 3) have a high degree of thermal matching with regard to the materials 57,92,122 to which it is affixed. In one exemplary and non-limiting embodiment the transition material 106 is formed with metal particles, where the metal can be silver, Nickel, Copper, and Aluminum and where the transition material 106 can be formed as a conductive ink containing the metal particles and a binder capable of maintaining the metal particles in an agglomerated state upon positioning on the array 56.

After application of the transition material 106 to the array 56, the array 56 and transition material 106 thereon are positioned within a suitable heating device (not shown) such as a furnace or kiln, in order to sinter the transition material 106 on the array 56. In performing the sintering, the binder present in the transition material 106 is removed while bonding the metal particles in the transition material 106 to the array 56, such as in one exemplary non-limiting embodiment to the periphery of a ceramic material forming the pixels 57. In this process, the metal particles effectively form a transition layer or grid 112 around the pixels 57 that is bonded securely to the pixels 57 and that provides a base for the attachment of the material 122 used to form the collimator plates 108 to the array 56.

Figure 9:
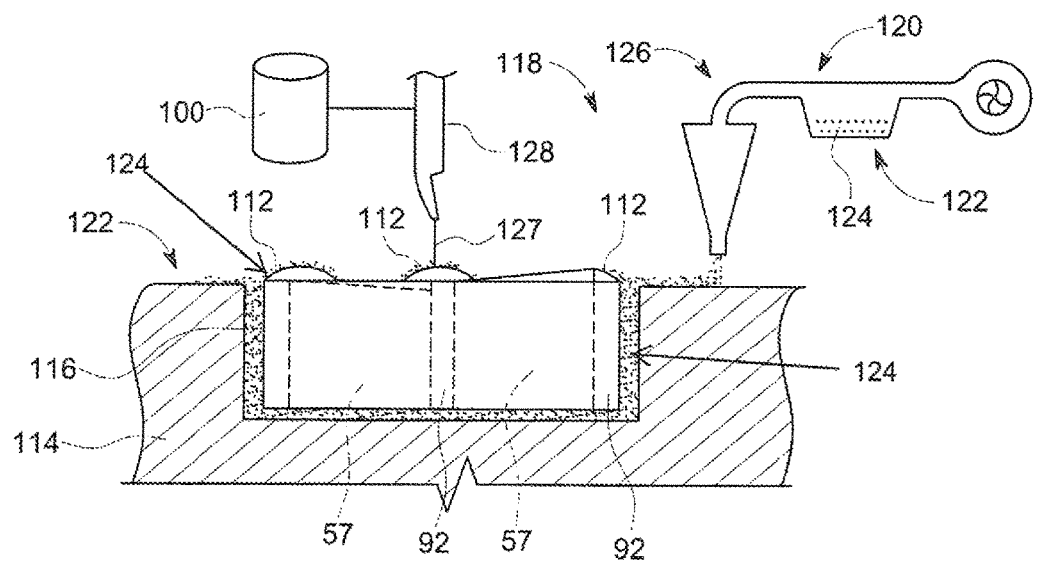
FIG. 9 is a schematic view of a method of application of a collimator plate material to a scintillator pack including a transition material layer according to an exemplary non-limiting embodiment of the invention.

After the sintering step is completed, as shown in FIG. 9 the pack/array 56 including the transition material layer or grid 112 thereon is transferred to tooling 114 including a recess 116 in which the array 56 is positioned. Within the recess 116, the data from the database 100 regarding the position to the pixels 57 is transferred to a direct laser metal sintering (DLMS)/additive manufacturing/metal 3D printing device 118. The device 118 includes a supply 120 of a material 122 used to form the collimator plates 108, such as tungsten powder 124 having a particle size of about 10 m, that is disposed on the tooling 114 within the recess 116 and over the pack 56 and pixels 57 by a re-coater 126 that traverses over the tooling 114 to dispense the material 122. The device 118 additionally includes a laser 128 that can be operated to direct a laser beam 127 at specified points on the array 56 as determined by the measurement data from the database 100 in order to weld the material 122 to the transition layer 112. In the DLMS process the laser can be controlled to be operated at different power levels depending upon the layer of the tungsten powder 124 being applied to the form the collimator plates 108. For example, the laser can be operated at low power during the initial phases where the first layers of the tungsten powder 124 are affixed to the silver transition layer 112 by only melting the silver transition layer 112 to bond to the tungsten material 124 After a sufficient number of layers of the tungsten material 124 have been bonded/welded to and built up on the transition material layer or grid 112 to space the tungsten powder 124 from the transition material layer 112, the laser 128 can be operated using the measurement data from database 100 at higher power levels to sinter or weld additional layers of tungsten material 124 to those tungsten layers already bonded to the transition layer 112 in order to build/print the collimator plates 108 to the desired height with respect to the array 56 and pixels 57 and form the scintillator/collimator assembly 90.

Figure 10:
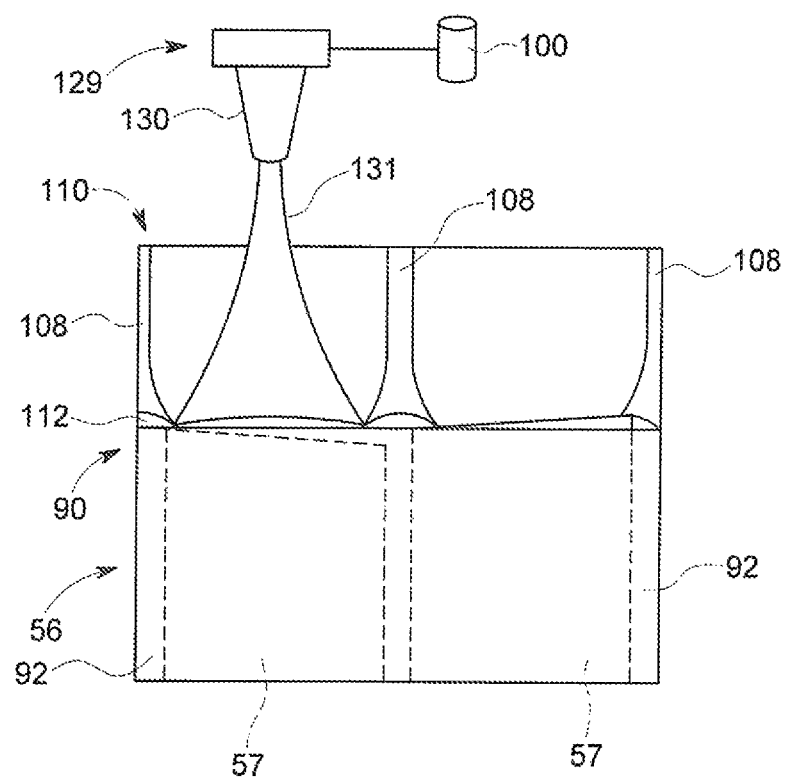
FIG. 10 is a schematic view of a method of application of a top reflective coating to a scintillator/collimator assembly according to one exemplary and non-limiting embodiment of the invention.

Upon reaching the desired height for the collimator plates 108, the assembly 90 can be removed from the tooling 104 and, as shown in FIG. 10, positioned within a suitable coating application device 129 capable of applying a reflective coating 131 to the pixels 57 within the collimator plates 108. Again, the pixel position data from database 100 is transferred to the device 129 in order to enable the device 126 to position an application nozzle 130 over the pixels 57 in order to apply the top reflective coating 131 directly onto the pixels 57 between the collimator plates 108 to provide the necessary light reflection for the pixels 57.

The adaptive manufacturing method and resulting structure of building/welding a two dimensional tungsten collimator directly to an array of scintillating pixels using 3D aerosol jet printing of a transition material 122 to the ceramic pixels 57 to form a base for the welding of the tungsten material solves the current problem of alignment of the collimator 110 between the x-ray focal spot and the individual detector components and dramatically reduces the number of parts in the detector assembly 90 thus eliminating cost, complexity and improving serviceability in the field. This method and resulting structure is facilitated by the initial optical measurement of the variation of the pixel array to accurately deposit the transition material layer 112 and collimator plate material 122 on the array 56 employing the data from the analysis of the scintillator array 56 as the direct datum used by the application devices 102,118,129 to place the various materials 106,122,131 precisely on the array 56. This, in turn, allows for the relaxing positional tolerances in the array 56 without degrading image quality and enable significant cost advantage due to the precise positioning of the collimator plates 108 on the array 56 using the optical measurement analysis of the array 56.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of manufacturing a detector having an integrated scintillator and collimator, the method comprising the steps of:
    applying a transition material to a scintillator array including scintillator pixels thereon to form a transition material layer on the scintillator array;
    applying a collimator material to the transition material layer in alignment with the scintillator pixels to form collimator plates on the scintillator array;
    wherein the pixels are formed of a ceramic and the transition material includes a metal bondable to a ceramic, and wherein the method further comprises the step of bonding the transition material layer to the ceramic pixels after applying the transition material to the scintillator array to form the transition material layer.

2. The method of claim 1 wherein the step of bonding the transition material layer to the ceramic pixels comprises sintering the transition material layer to the ceramic pixels.

3. The method of claim 1 further comprising the step of applying a reflective coating onto the pixels after applying the collimator material.

4. A method of manufacturing a detector having an integrated scintillator and collimator, the method comprising the steps of:
    applying a transition material to a scintillator array including scintillator pixels thereon to form a transition material layer on the scintillator array;
    applying a collimator material to the transition material layer in alignment with the scintillator pixels to form collimator plates on the scintillator array;
    conducting an optical measurement analysis of the scintillator pixels on the array prior to applying the transition material; and
    storing data on the location of the pixels on the scintillator array in a database.

5. The method of claim 4 wherein the step of conducting the optical measurement analysis comprises determining the precise position and pitch of each scintillator pixel on the scintillator array.

6. The method of claim 4 wherein the step of applying the transition material comprises the steps of:
    accessing the data on the location of the pixels on the scintillator array; and
    directing a transition material application device using the data on the location of the pixels.

7. The method of claim 6 wherein step of directing the transition material application device comprises applying the transition material to a perimeter of each pixel.

8. The method of claim 6 wherein the transition material application device is an aerosol jet printer.

9. The method of claim 6 wherein the step of applying the collimator material comprises the steps of:
    accessing the data on the location of the pixels on the scintillator array; and
    directing a collimator material application device using the data on the location of the pixels.

10. The method of claim 9 wherein step of directing the collimator material application device comprises applying the collimator material to a perimeter of each pixel over the transition material layer.

11. The method of claim 10 wherein the step of applying the collimator material to the transition layer comprises printing the collimator material onto the transition material layer.

12. The method of claim 11 wherein the step of printing the collimator material onto the transition material layer comprise direct laser sintering the collimator material onto the transition material layer.

13. The method of claim 12 wherein the step of direct laser sintering the collimator material onto the transition material layer comprises the step of varying the power of the laser applied to the collimator material in relation to the distance of the collimator material from the transition material layer.

14. The method of claim 13 wherein the step of varying the power of the laser comprises:
    applying a low power laser to the collimator material close to the transition material layer; and
    applying a high power laser to collimator material spaced from the transition material layer.

15. A detector comprising:
    an array of scintillation pixels;
    a transition material layer bonded to the pixels; and
    a plurality of collimator plates bonded to the transition material layer, wherein the transition material layer is sintered to the pixels.

16. The detector of claim 15 wherein the transition material layer is formed of silver.

17. An imaging system comprising:
   an x-ray source;
   a control mechanism operably connected to the x-ray source; and
   a detector operably connected to the control mechanism, the detector including a scintillator/collimator assembly having an array of scintillation pixels, a transition material layer bonded to the pixels and a plurality of collimator plates bonded to the transition material layer, wherein the transition material layer is sintered to the pixels.

18. The imaging system of claim 17 wherein imaging system is a CT imaging system.

* * * * *